（12）United States Patent
Eisenhauer

(10) Patent No.: US 9,968,040 B2
(45) Date of Patent: May 15, 2018

(54) PLANT POLLINATION COVER BAG

(71) Applicant: David Joseph Eisenhauer, Sebastopol, CA (US)

(72) Inventor: David Joseph Eisenhauer, Sebastopol, CA (US)

(*) Notice: Subject to any disclaimer, the term of this patent is extended or adjusted under 35 U.S.C. 154(b) by 108 days.

(21) Appl. No.: 15/283,376

(22) Filed: Oct. 1, 2016

(65) Prior Publication Data
US 2018/0092315 A1  Apr. 5, 2018

(51) Int. Cl.
*A01H 1/02*  (2006.01)
*B65D 33/28*  (2006.01)
*A01G 7/00*  (2006.01)

(52) U.S. Cl.
CPC .............. *A01H 1/025* (2013.01); *A01G 7/00* (2013.01); *B65D 33/28* (2013.01)

(58) Field of Classification Search
CPC .. A01H 1/025; A01G 7/00; B65C 3/28; A24F 23/02; B65D 33/14; B65D 5/2057; B65D 25/087; B65D 33/2591; B65D 75/5811
USPC ........... 47/1.41; 424/464; 206/423; 383/206, 383/39
See application file for complete search history.

(56) References Cited

U.S. PATENT DOCUMENTS

| | | | | |
|---|---|---|---|---|
| 3,962,821 A * | 6/1976 | Sharp | ...................... | A01H 1/025 222/161 |
| 4,554,761 A * | 11/1985 | Tell | ........................ | A01H 1/025 47/1.41 |
| 5,439,100 A * | 8/1995 | Gordon | ..................... | A61L 9/12 206/204 |
| 6,647,697 B1 * | 11/2003 | Zarrow | .................. | B65D 33/14 206/461 |
| 6,935,492 B1 * | 8/2005 | Loeb | .................. | B65D 81/3272 206/219 |
| 7,607,256 B2 * | 10/2009 | Iwig | ........................ | A01H 1/02 47/1.41 |
| 2002/0086806 A1 * | 7/2002 | Giblin | ................ | B65D 75/5811 510/296 |
| 2003/0231808 A1 * | 12/2003 | Machacek | .......... | B65D 33/2591 383/36 |

(Continued)

*Primary Examiner* — Albert Wong

(57) ABSTRACT

A plant pollination bag including a bag made of a flexible material, a pouch formed out of one or more additional pieces of material fixed to the wall of the bag, where a space is created between the at least one additional piece of material and the wall of the bag; at least one of a releasable closure and a tear line fixed to the one or more additional pieces of material and the wall of the bag, where the one or more of a releaseable closure and a tear line is adapted to seal the space between the one or more additional pieces of material and the wall of the bag; an elongated piece of material attached to the at least one of a releasable closure and a tear line, where the elongated piece of material is designed to extend from the interior of the bag to a location outside of the bag, where the elongated piece of material is further adapted to allow a user to at least one of A) open the releasable closure and B) tear the tear line from outside of the bag. The system of the preferred embodiments is preferably designed to one or more of assist in the pollination of a plant, capture seeds dropped by the plant, and prevent cross-pollination of the plant by unintended plants.

15 Claims, 1 Drawing Sheet

(56) References Cited

U.S. PATENT DOCUMENTS

| | | | |
|---|---|---|---|
| 2006/0023976 A1* | 2/2006 | Alvater | B65D 75/5805 383/210 |
| 2006/0191805 A1* | 8/2006 | Vogel | B65D 25/087 206/222 |
| 2009/0065605 A1* | 3/2009 | Roche | A47G 21/18 239/33 |
| 2009/0233252 A1* | 9/2009 | Cinader, Jr. | A61C 7/14 433/9 |
| 2014/0044381 A1* | 2/2014 | Ulstad | B65D 5/2057 383/207 |
| 2016/0037740 A1* | 2/2016 | De La Sotta | A01G 22/00 47/1.41 |

* cited by examiner

PLANT POLLINATION COVER BAG

DESCRIPTION OF THE PREFERRED EMBODIMENTS

The description that follows of the invention's preferred embodiments is meant to enable someone skilled in the prior art to make and use the invention, but is not meant to limit the invention to these preferred embodiments.

1. First Preferred Embodiment

Figure 1:
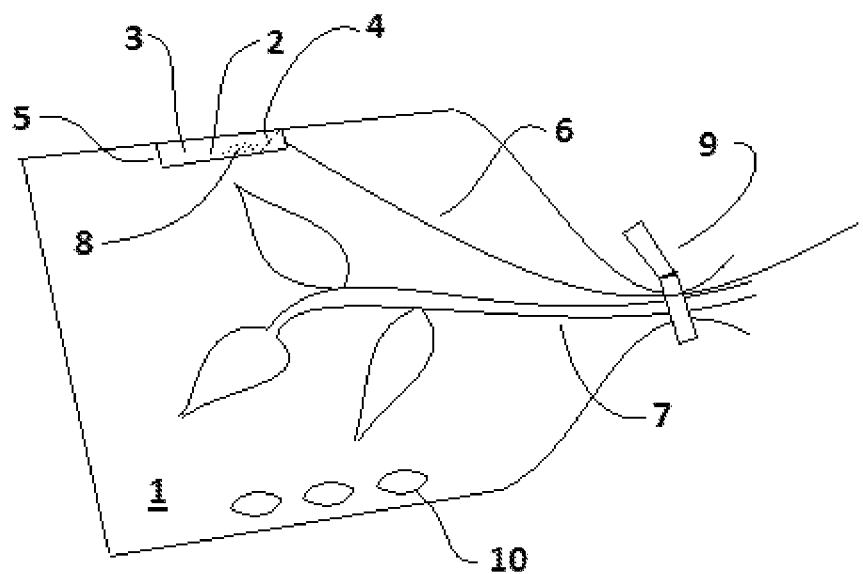
FIG. 1 is a schematic representation of the system of the first preferred embodiments.

As shown in FIG. 1, the system 7 of the preferred embodiments is a plant 7 pollination bag 1 including a bag 1 made of a flexible material, a pouch 2 formed out of one or more additional pieces of material fixed to the wall of the bag 1, where a space 3 is created between the at least one additional piece of material 5 and the wall of the bag 1; at least one of a releasable closure 4 and a tear line 4 fixed to the one or more additional pieces of material and the wall of the bag 1, where the one or more of a releaseable closure 4 and a tear line 4 is adapted to seal the space 3 between the one or more additional pieces of material and the wall of the bag 1; an elongated piece of material 6 attached to the at least one of a releasable closure 4 and a tear line 4, where the elongated piece of material 6 is designed to extend from the interior of the bag 1 to a location outside of the bag 1, where the elongated piece of material 6 is further adapted to allow a user to at least one of A) open the releasable closure 4 and B) tear the tear line 4 from outside of the bag 1. The system 7 of the preferred embodiments is preferably designed to one or more of assist in the pollination of a plant 7, capture seeds 10 dropped by the plant 7, and prevent cross-pollination of the plant 7 by unintended plant 7s. The system 7 of the preferred embodiments may, however, be used for any suitable purpose.

As shown in FIG. 1, the system 7 of the preferred embodiments includes a bag 1 made of flexible material, where the bag 1 is designed to fit over at least one of a branch 7, a stem 7, a flower 7, and a portion of a plant 7. The bag 1 is preferably made out of a material including but not limited to polyethylene, cotton, wool, polyvinyl, another flexible polymer sheet material, nylon fabric, and another fabric material. The bag 1 may, however, be constructed out of any suitable material. Preferably the bag 1 can be constricted using a cinch closure 9 to at least partially close off the opening once it is placed over the branch 7, stem 7, flower 7, or other portion of the plant 7. The cinch closure 9 may be a zip tie placed around the bag 1, a string or cord tied around the bag 1, a drawstring in a channel around the rim of the bag 1, at least one spring clamp, velcro, a zipper, tape, an elastic cord, an elastic ring or band, or any other suitable form of closure. In some variations there may not be a cinch closure 9. In a preferred variation, the bag 1 may be adapted to be easily written on with a writing utensil so that information regarding the generating the seeds 10 and the plant 7 that generated the pollen 8 can be recorded on the bag 1 that will contain the seeds 10. There may, however, be any suitable form of record keeping or none at all.

As shown in FIG. 1, the bag 1 includes at least one additional piece of material 5 attached to the inside wall of the bag 1, forming a pouch 2 and creating a space 3 between the at least one additional piece of material 5 and the bag 1 wall. As shown in FIG. 1, at least one of a releasable closure 4 and a tear line 4 is included to seal the opening of the pouch 2, meaning the opening of the space 3 between the at least one additional piece of material 5 and the wall of the bag 1. The at least one of a releasable closure 4 and a tear line 4 is preferably adapted to retain contents inside the pouch 2, such as at least one of powder, granular contents, and liquid content, and which in one variation may include pollen 8. In one preferred variation, the releasable closure 4 can be a flap of material with a temporary adhesive that sticks the flap of material to at least one of the bag 1 wall and the pouch 2 to seal the opening of the pouch 2. In another preferred variation, the releasable closure 4 can be a flap of material with any other form of temporary attachment fastener to temporarily attach the flap of material to at least one of the bag 1 wall and the pouch 2, where the temporary attachment fastener can include a hook and loop fastener, a snap fastener, and any other suitable temporary attachment fastener. There may, however, be any suitable means of temporarily sealing the pouch 2.

As shown in FIG. 1, there is preferably a elongated piece of material 6 attached to the at least one of a releasable closure 4 and a tear line 4, and this elongated piece of material 6 preferably extends from the interior of the bag 1 to a position external to the bag 1. This preferably allows a user to grasp the external end of the elongated piece of material 6, which preferably allows the user to use the elongated piece of material 6 to open the at least one of a releasable closure 4 and a tear line 4. In one preferred variation, the elongated piece of material 6 is at least one of a wire, a string, a piece of cord, a rod, and any other suitable piece of material for activating the at least one of a releasable enclosure 4 and a tear line 4. In one preferred variation, the elongated piece of material 6 is used to tear the tear line 4 that seals the pouch 2. In another preferred embodiment, squeezing the pouch 2 from the outside opens the releasable closure 4. There may, however, be any suitable means of opening the at least one of a releasable closure 4 and a tear line 4.

As shown in FIG. 1, in a preferred embodiment the pouch 2 is loaded with pollen 8. Preferably when the elongated piece of material 6 is grasped by the user it can be used to open the pouch 2 and release the pollen 8 into the interior of the pollination bag 1. Preferably this contains the pollen 8 and increases the chances of pollination by that particular pollen 8, which greatly increases the ability to control which plant 7 strains are combined and the lineage of plant 7s created. Preferably the bag 1 also keeps out outside pollen 8 from other plant 7s, preventing unintended and uncontrolled pollination. The pouch 2 may, however, be loaded with any suitable contents. The bag 1 may, however, serve any suitable purpose.

Figure 2:
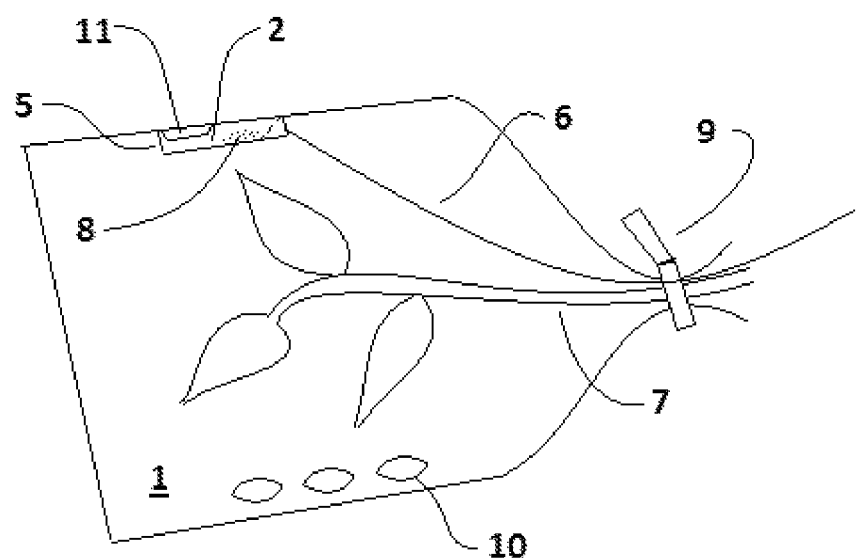
FIG. 2 is a schematic representation of the system of the first preferred embodiments, wherein a sealable opening is included in the wall of the bag.

As shown in FIG. 2, in a preferred variation a sealable opening 11 is included in the outer wall of the bag 1 and aligned with the space 3 inside the pocket, so that contents can be loaded into the pouch 2 from outside the bag 1 and then sealed in. The sealable opening 11 may be sealed by a flap of material with an adhesive to seal the flap. In an alternate variation the sealable opening 11 may seal with a zip-lock bag type closure or with a hook and loop fastener. The opening may, however, be sealed by any suitable closure 4.

As shown in FIG. 1, the bag 1 preferably catches seeds 10 that develop and fall off of the plant 7. This makes seed 10 collection easier for the user and also promotes keeping the seeds 10 organized by lineage and other suitable factors. The bag 1 may, however, be used for any suitable purpose.

As a person skilled in the art will recognize from the previous detailed description and from the figures and claims, modifications and changes can be made to the preferred embodiments of the invention without departing from the scope of this invention defined in the following claims.

I claim:

1. A plant pollination bag, comprising:
    a bag made of a flexible material and having an inner surface, an outer surface, and an opening;
    a piece of material fixed to the inner surface of the bag to form a pouch by forming a space between the inner surface of the bag and the piece of material;
    a releasable closure or a tear line fixed to the inner surface of the bag or the piece of material to seal the pouch from the interior of the bag; and
    an elongated piece of material attached to the releasable closure or the tear line, wherein the elongated piece of material is attached to the releasable closure or the tear line and extends through the opening of the bag to a location outside the bag, wherein the elongated piece of material allows the user to open the releasable enclosure or to tear the tear line to expose the pouch to the interior of the bag without reaching inside the bag or when the opening is closed, by pulling on the piece of material.

2. The plant pollination bag of claim 1, wherein the bag is adapted to fit over at least one of a branch, a stem, and a portion of a plant.

3. The plant pollination bag of claim 2, wherein the pouch is filled with pollen.

4. The plant pollination bag of claim 3, wherein the elongated piece of material is used by a user to release the pollen into the interior of the pollination bag.

5. The plant pollination bag of claim 1, wherein the pouch is filled with pollen.

6. The plant pollination bag of claim 5, wherein the elongated piece of material is used by a user to release the pollen into the interior of the pollination bag.

7. The plant pollination bag of claim 1, further comprising a cinch closure attached to the opening of the pollination bag, wherein the cinch closure is adapted to tighten the opening of the pollination bag.

8. The plant pollination bag of claim 2, further comprising a cinch closure attached to the opening of the pollination bag, wherein the cinch closure is adapted to tighten the opening of the pollination bag.

9. The plant pollination bag of claim 4, further comprising a cinch closure attached to the opening of the pollination bag, wherein the cinch closure is adapted to tighten the opening of the pollination bag.

10. The plant pollination bag of claim 6, further comprising a cinch closure attached to the opening of the pollination bag, wherein the cinch closure is adapted to tighten the opening of the pollination bag.

11. The plant pollination bag of claim 3, further comprising a sealable opening in the wall of the pollination bag, wherein the sealable opening allows a user to load pollen into the pouch from the exterior of the bag and then seal the pollen into the pouch.

12. The plant pollination bag of claim 4, further comprising a sealable opening in the wall of the pollination bag, wherein the sealable opening allows a user to load pollen into the pouch from the exterior of the bag and then seal the pollen into the pouch.

13. The plant pollination bag of claim 6, further comprising a sealable opening in the wall of the pollination bag to allow a user to load pollen from the exterior of the bag.

14. The plant pollination bag of claim 13, wherein the elongated piece of material is at least one of a string and a wire.

15. The plant pollination bag of claim 14, wherein the cinch closure is a zip tie.

* * * * *